United States Patent [19]

Acker et al.

[11] 4,371,525
[45] Feb. 1, 1983

[54] SILYL-BENZIMIDAZOLE-2-CARBAMIC ACID ESTERS AND THEIR USE AS FUNGICIDES

[75] Inventors: Rolf-Dieter Acker, Leimen; Karl-Heinz Koenig, Frankenthal; Gerhard Hamprecht, Weinheim; Ernst-Heinrich Pommer, Limburgerhof, all of Fed. Rep. of Germany

[73] Assignee: BASF Aktiengesellschaft, Fed. Rep. of Germany

[21] Appl. No.: 208,034

[22] Filed: Nov. 18, 1980

[30] Foreign Application Priority Data

Dec. 4, 1979 [DE] Fed. Rep. of Germany ....... 2948672

[51] Int. Cl.$^3$ .................... A01N 55/00; C07F 7/10
[52] U.S. Cl. ...................................... 424/184; 548/110
[58] Field of Search ................. 548/110, 306; 424/184

[56] References Cited

U.S. PATENT DOCUMENTS

| | | | |
|---|---|---|---|
| 2,906,756 | 9/1959 | de Benneville et al. ............ | 548/110 |
| 4,046,770 | 9/1977 | Paget et al. ......................... | 548/110 |
| 4,136,174 | 1/1979 | Haugwitz et al. .................. | 424/184 |

OTHER PUBLICATIONS

Birkofer et al., Chem. Abst., 1961, vol. 55, pp. 5484-5485.
R. Wegler, Chemie der Pflanzenschutz- und Schädlingsbekämp- fungsmittel, vol. 4, p. 175, Springer-Verlag, Berlin, (1977).

*Primary Examiner*—Henry R. Jiles
*Assistant Examiner*—Natalia Harkaway
*Attorney, Agent, or Firm*—Keil & Witherspoon

[57] ABSTRACT

Silyl-benzimidazole-2-carbamic acid esters of the formula I

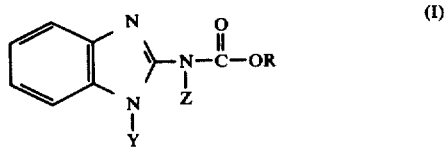

where Y and Z are hydrogen or a silyl radical of the formula

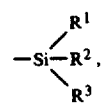

where $R^1$, $R^2$ and $R^3$ independently of one another are unsubstituted or halogen-substituted alkyl, alkenyl or alkynyl of up to 12 carbon atoms, cycloalkyl of up to 7 carbon atoms which is unsubstituted or substituted by alkyl or alkynyl of up to 4 carbon atoms, or phenyl which is unsubstituted or substituted by halogen or alkyl of up to 4 carbon atoms, and R is alkyl of up to 4 carbon atoms, with the proviso that Y and Z are not both hydrogen, and their use as fungicides.

The new active ingredients are particularly suitable for combating harmful phycomycetes, ascomycetes and fungi imperfecti.

10 Claims, No Drawings

SILYL-BENZIMIDAZOLE-2-CARBAMIC ACID ESTERS AND THEIR USE AS FUNGICIDES

The present invention relates to novel silyl-benzimidazole-2-carbamic acid esters, their preparation, fungicides which contain these compounds as active ingredients, and processes for combating fungi with these compounds.

The use of benzimidazole-carbamic acid esters as fungicides in agriculture and horticulture has been disclosed (R. Wegler, Chemie der Pflanzenschutz- und Schädlingsbekämpfungsmittel, Volume 4, page 180 et seq., Springer-Verlag, Berlin, 1977). These known compounds are systemically highly active against a range of fungal diseases. However, their shortcoming is that they are sparingly soluble in many solvents, which restricts their use, for example in timber preservation.

We have found that the novel silyl-benzimidazole-2-carbamic acid esters of the general formula (I)

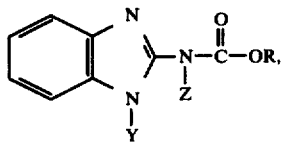

where Y and Z are hydrogen or a silyl radical of the formula

where $R^1$, $R^2$ and $R^3$ independently of one another are unsubstituted or halogen-substituted alkyl, alkenyl or alkynyl of up to 12 carbon atoms, cycloalkyl of up to 7 carbon atoms which is unsubstituted or substituted by alkyl or alkynyl of up to 4 carbon atoms, or phenyl which is unsubstituted or mono- or polysubstituted by halogen or alkyl of up to 4 carbon atoms, and R is alkyl of up to 4 carbon atoms, with the proviso that Y and Z are not both hydrogen, exhibit a substantially better fungicidal action than conventional benzimidazole-carbamic acid esters. The novel compounds are particularly suitable for combating harmful phycomycetes, ascomycetes and fungi imperfecti.

In formula I, R is unbranched or branched alkyl of 1 to 4 carbon atoms, eg. methyl, ethyl, n-propyl, isopropyl, n-butyl, isobutyl or tert.-butyl.

In the silyl radicals Y and Z in formula I, $R^1$, $R^2$ and $R^3$ are linear or branched, unsubstituted or halogen-substituted, alkyl of 1 to 12 carbon atoms, preferably of 1 to 4 carbon atoms, linear or branched, unsubstituted or halogen-substituted, alkenyl or alkynyl of up to 12 carbon atoms, preferably of 3 or 4 carbon atoms, cycloalkyl of 3 to 7 carbon atoms which is unsubstituted or substituted by alkyl or alkynyl of up to 4 carbon atoms, or phenyl which is unsubstituted or substituted by halogen or alkyl of up to 4 carbon atoms. Examples of these substituents $R^1$, $R^2$ and $R^3$ are methyl, ethyl, n-propyl, isopropyl, n-butyl, isobutyl, tert.-butyl, n-pentyl, 1-methyl-n-butyl, 1-ethyl-n-propyl, neopentyl, tert.-amyl, 2-methyl-n-butyl, 3-methyl-n-butyl, isoamyl, n-hexyl, 1,3-dimethyl-n-butyl, 2,3-dimethyl-n-butyl, 1,1-dimethyl-n-butyl, 1-methyl-n-pentyl, 1-ethyl-n-butyl, 1,2-dimethyl-n-butyl, 3-methyl-n-pentyl, 1-methyl-1-ethyl-n-propyl, 4,4-dimethyl-n-butyl, n-heptyl, 1-methyl-n-hexyl, 1-ethyl-n-hexyl, 1-n-propyl-n-butyl, n-octyl, 1-methyl-n-heptyl, 1-ethyl-n-heptyl, 1-n-propyl-n-pentyl, 1-methyl-4-ethyl-n-hexyl, 3-methyl-1-isobutyl-n-butyl, 1-isobutyl-4-ethyl-n-hexyl, 1-ethyl-neopentyl, 1,2-dimethyl-n-hexyl, 1-methyl-4-ethyl-n-octyl, n-nonyl, n-decyl, n-undecyl, n-dodecyl, 1,4-diethyl-n-octyl, 1,4-diethyl-n-hexyl, 1,1-dimethylisobutyl, 1,1-dimethyl-n-pentyl, 1,1-diethyl-n-propyl, 1-methyl-1-ethyl-n-butyl, 1-methyl-1-ethyl-isobutyl, 1,1-dimethyl-isoamyl, 1,1-dimethyl-neopentyl, 1,1-dimethyl-n-hexyl, 1-n-propyl-1-methyl-n-butyl, 1,1,3-trimethyl-n-pentyl, 1,1-dimethyl-n-heptyl, cyclopropyl, cyclobutyl, cyclopentyl, cyclohexyl, cycloheptyl, 1-methyl-cyclopentyl, 1-methyl-cyclohexyl, 1-ethyl-cyclohexyl, 1-ethynyl-cyclohexyl, vinyl, allyl, methallyl, crotyl, 2-ethyl-n-hex-2-enyl, n-hex-5-enyl, n-undec-10-enyl, 2-methyl-but-2-enyl, 1-methyl-isobut-2-enyl, 1-methyl-n-prop-2-ynyl, n-but-2-ynyl, 1-methyl-n-prop-2-enyl, n-prop-2-ynyl, 3-methyl-n-but-3-enyl, 3-methyl-n-but-2-enyl, 1,1-dimethyl-n-prop-2-enyl, phenyl, o-, m- and p-tolyl, o-, m- and p-ethylphenyl, o-, m- and p-propylphenyl, o-, m- and p-isopropylphenyl, o-, m- and p-butylphenyl, o-, m- and p-isobutylphenyl, o-, m- and p-tert.-butylphenyl and o-, m- and p-chlorophenyl.

The novel silyl-benzimidazole-2-carbamic acid esters of the formula I are obtained by reacting a benzimidazole-carbamic acid ester of the formula II

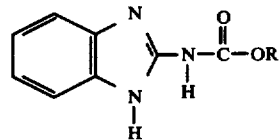

where R has the above meanings, or an alkali metal salt or alkaline earth metal salt of such an ester, with a halosilane of the formula III

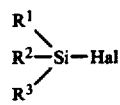

where $R^1$, $R^2$ and $R^3$ have the above meanings and Hal is halogen, in the presence of an inert diluent and in the presence or absence of an acid acceptor.

If the sodium salt of methyl benzimidazole-2-carbamate and triethylchlorosilane are used as starting materials, the course of the reaction, in the process according to the invention, may be represented by the following equation:

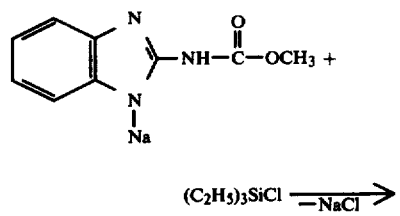

-continued

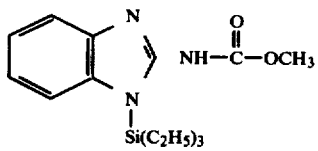

If the bis-lithium salt of methyl benzimidazole-2-carbamate and n-butyl-dimethylchlorosilane are used as starting materials, the course of the reaction, in the process according to the invention, may be represented by the following equation:

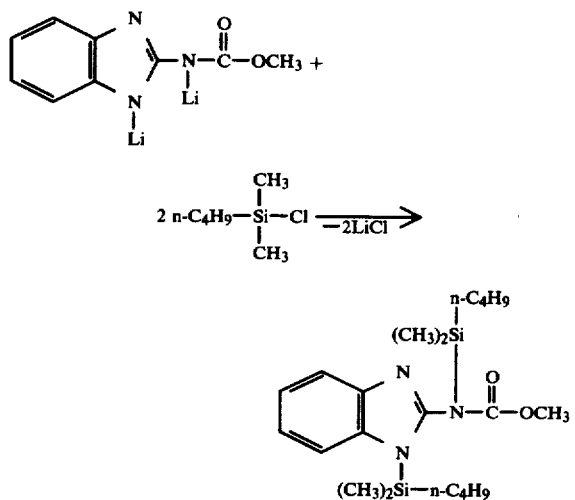

Examples of inert diluents which may be used in the process include acylamides, e.g. dimethylformamide and dimethylacetamide; nitriles, e.g. acetonitrile, benzonitrile and butyronitrile; sulfoxides, eg. dimethylsulfoxide; phosphoric acid amides, eg. hexamethylphosphorotriamide; ketones, eg. acetone, methyl ethyl ketone, cyclohexanone and acetophenone; ethers, eg. tetrahydrofuran, anisole, dimethoxyethane, n-butyl ethyl ether and dioxane; nitroalkanes, eg. nitromethane; nitrobenzene; ureas, eg. tetramethylurea; sulfones, eg. sulfolane; esters, eg. methyl acetate, methyl propionate and methyl formate; halohydrocarbons, especially chlorohydrocarbons, eg. methylene chloride, chloroform, 1,2-dichloroethane, 1,1,2,2- and 1,1,1,2-tetrachloroethane; dichloropropane, trichloroethylene, chlorobenzene, o-, m- and p-dichlorobenzene, fluorobenzene, o-, m- and p-chlorotoluene, dichloronaphthalene and carbon tetrachloride; aliphatic and cycloaliphatic hydrocarbons, eg. heptane, pinane, gasoline fractions boiling within a range of from 70° to 190° C., cyclohexane, methylcyclohexane, decalin, petroleum ether, naphtha, 2,2,4-trimethylpentane and octane; aromatic hydrocarbons, eg. benzene, toluene, o-, m- and p-cymene o-, m- and p-xylene and tetralin; and mixtures of the above. Advantageously, the solvent is used in an amount of from 100 to 2,000% by weight, preferably from 100 to 1,000% by weight, based on the starting compound of the formula II.

Examples of suitable acid acceptors are alkali metals, alkali metal hydrides, alkali metal alcoholates, alkaline earth metal alcoholates, organo-metallic compounds and tertiary organic amines. Particularly suitable acid acceptors are lithium, lithium hydride, sodium hydride, potassium hydride, calcium hydride, phenyl-lithium, n-butyl-lithium, methyl-lithium, sodium methylate, magnesium ethylate, methyl-magnesium bromide, ethyl-magnesium bromide, phenyl-magnesium bromide, phenyl-magnesium chloride, potassium methylate, sodium propylate, aluminum isopropylate, sodium butylate, lithium methylate, calcium cyclohexanolate, sodium propylate, potassium tert.-butylate, trimethylamine, triethylamine, tripropylamine, triisopropylamine, tributylamine, triisobutylamine, tri-sec.-butylamine, tri-tert.-butylamine, tribenzylamine, tricyclohexylamine, triamylamine, trihexylamine, N,N-dimethylaniline, N,N-diethylaniline, N,N-diisopropylaniline, N,N-dimethyltoluidine, N,N-diethyltoluidine, N,N-dipropyltoluidine, 4-N,N-dimethylaminopyridine, 4-N,N-diethylamino-pyridine, N-methylpiperidine, N-ethylpiperidine, N-methylpyrrolidine, N-ethylpyrrolidine, N-methylpyrrole, N-methylmorpholine, N-ethylmorpholine, N-methylhexamethyleneimine, pyridine, quinoline, α-, β- and γ-picoline, acridine, N,N,N',N'-tetramethylethylenediamine, N-ethyldiisopropylamine and N,N-dimethylcyclohexylamine. However, other conventionally used basic compounds may also be employed.

It can be advantageous to carry out the reaction in the presence of a conventional reaction accelerator for silylation reactions. Examples of suitable accelerators are imidazole and 4-dimethylamino-pyridine.

The reaction is in general carried out at from −70° to 100° C., preferably from −20° to +100° C., for from 30 minutes to 200 hours, preferably from 1 hour to 100 hours, under atmospheric or superatmospheric pressure, batchwise or continuously. In general, from 0.5 to 2 moles, preferably from 0.9 to 1.5 moles, of the compound of the formula III, with or without from 0.5 to 2 moles of the acid acceptor, are employed, per mole of compound of the formula II, in the preparation of the monosilyl compounds of the formula I. If an alkali metal, an alkali metal hydride, an alkali metal alcoholate or an alkaline earth metal alcoholate is used as the acid acceptor, it is possible first to convert the compound of the formula II into its alkali metal salt or alkaline earth metal salt and to employ it in this form. To prepare the bis-silyl compounds of the formula I, from 1 to 4 moles, preferably from 1.8 to 3 moles, of the compound of the formula III are used per mole of compound of the formula II.

To avoid losses of silyl chloride from hydrolysis, it is advisable to carry out the reaction in the presence of a protective gas, for example nitrogen or argon.

In a preferred procedure, the chlorosilane of the formula III is added in portions to a suspension of the compound of the formula II in a suitable solvent; however, it is also possible to add the suspension of the ester in portions to the chlorosilane.

The end products of the formula I may be isolated by evaporating the solvent and filtering off insoluble matter; the compound of the formula I then crystallizes from the residue. This compound may also be further purified by taking it up in a solvent, eg. tetrahydrofuran, chloroform or cyclohexane, filtering the solution and removing the solvent under reduced pressure. Chromatographic purification is also possible.

The esters of the formula II, and processes for their preparation, are disclosed in R. Wegler, Chemie der Pflanzenschutz- und Schädlingsbekämpfungsmittel, Volume 4, pages 180–185, Springer-Verlag, Berlin, 1977. The halosilanes of the formula III may be prepared by conventional methods (V. Bazant et al., Organosilicon Compounds, Volume 2/1, Academic Press, New York, 1965).

The Examples which follow illustrate the preparation of the silyl-benzimidazole-2-carbamic acid esters of the formula I. Parts are by weight.

EXAMPLE 1

3.5 parts of n-butyl-lithium in hexane are added in portions to a suspension of 10 parts of methyl benzimidazole-2-carbamate in 130 parts of absolute tetrahydrofuran at −78° C., under nitrogen. The mixture is then warmed to room temperature and stirred for 5 hours, after which 8.2 parts of triethylchlorosilane are added in portions. After stirring for 12–15 hours, insoluble matter is filtered off and the solvent is removed under reduced pressure. 4.5 parts of methyl N-triethylsilyl-benzimidazole-2-carbamate crystallize out from the residue; decomposition point >120° C. (active ingredient No. 1). NMR ($\delta$ in ppm): 0.4–1.5 (15H, Si($C_2H_5$)$_3$); 3.70 (3H, $OCH_3$); 6.7–7.5 (4H, aromatic).

EXAMPLE 2

A solution prepared from 4 parts of sodium in 40 parts of methanol is added, in portions, to a suspension of 30 parts of methyl benzimidazole-2-carbamate in 200 parts of dioxane. The mixture is refluxed for 2 hours, the solvent is distilled off under reduced pressure and the residue is dried thoroughly.

5 parts of the resulting sodium salt of methyl benzimidazolecarbamate are suspended in 15 parts of dimethylformamide and 3.9 parts of triethylchlorosilane are added, in portions, at room temperature. After stirring the mixture for 12 hours under nitrogen, the solvent is distilled off under reduced pressure, tetrahydrofuran is added to the residue, and the solution is filtered. The solvent is then distilled off, giving 2.7 parts of methyl N-triethylsilyl-benzimidazole-2-carbamate; decomposition point >120° C. (active ingredient No. 1).

EXAMPLE 3

5.0 parts of the sodium salt described in Example 2 and 4.0 parts of triethylchlorosilane are mixed in 120 parts of tetrahydrofuran at room temperature, under nitrogen. The mixture is stirred for 12 hours and then filtered. On distilling the solvent from the filtrate, 3.2 parts of methyl N-triethylsilyl-benzimidazole-2-carbamate are obtained; decomposition point >120° C. (active ingredient No. 1).

EXAMPLE 4

4.1 parts of triethylchlorosilane and 3.0 parts of triethylamine are separately added, in portions, to 5 parts of methyl benzimidazole-2-carbamate in 50 parts of tetrahydrofuran. After 12 hours, the mixture is filtered and the solvent is distilled from the filtrate under reduced pressure. 1.6 parts of methyl N-triethylsilyl-benzimidazole-2-carbamate are obtained; decomposition point >120° C. (active ingredient No. 1).

EXAMPLE 5

3.5 parts of n-butyl-lithium in hexane are added, in portions, to a suspension of 10 parts of methyl benzimidazole-2-carbamate in 100 parts of absolute tetrahydrofuran, under nitrogen at −78° C. The mixture is warmed to room temperature and stirred for 6 hours, after which 9.5 parts of n-butyl-dimethylchlorosilane are added in portions. After stirring for 12 hours, insoluble matter is filtered off and the solvent is removed from the filtrate under reduced pressure. 9.0 parts of methyl N-dimethyl-n-butylsilyl-benzimidazole-2-carbamate remain in the residue; decomposition point >110° C. (active ingredient No. 2). NMR ($\delta$ in ppm): 0.5–1.8 (n-$C_4H_9$($CH_3$)$_2$Si, 15H); 3.60 ($OCH_3$, 3H); 6.7–7.6 (aromatic, 4H).

EXAMPLE 6

5 parts of methyl benzimidazole-2-carbamate are suspended in 80 parts of absolute tetrahydrofuran. 1.8 parts of n-butyl-lithium in hexane are added, in portions, at −78° C., under nitrogen. The mixture is stirred for 2 hours at 0° C. and a further 1.8 parts of n-butyl-lithium in hexane are then added in portions at −78° C. After stirring this mixture for 2 hours at 0° C., 9 parts of n-butyl-dimethylchlorosilane are added in portions. The resulting mixture is stirred for 12 hours at room temperature, insoluble matter is filtered off, and the solvent is removed under reduced pressure. 8.7 parts of methyl N,N'-bis-(n-butyl-dimethylsilyl)-benzimidazole-2-carbamate are obtained (active ingredient No. 3).

NMR ($\delta$ in ppm): 0.5–1.6 (n-$C_4H_9$($CH_3$)$_2$Si, 30H); 3.32 ($OCH_3$, 3H); 6.6–7.5 (aromatic, 4H).

For instance the following compounds of the formula I may be prepared analogously:

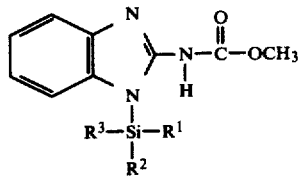

| No. | $R^1$ | $R^2$ | $R^3$ | NMR data ($\delta$ in ppm) | | |
|---|---|---|---|---|---|---|
| | | | | Si$R^1R^2R^3$ | $OCH_3$ | aromatic |
| 4 | $CH_3$ | $CH_3$ | t-$C_4H_9$ | 0.70; 1.00 | 3.80 | 6.7–7.5 |
| 5 | $CH_3$ | $CH_3$ | $C_2H_5$ | | | |
| 6 | $CH_3$ | $CH_3$ | n-$C_3H_7$ | | | |
| 7 | $CH_3$ | n-$C_3H_7$ | n-$C_3H_7$ | | | |
| 8 | $CH_3$ | $CH_3$ | i-$C_3H_7$ | | | |
| 9 | $CH_3$ | i-$C_3H_7$ | i-$C_3H_7$ | | | |
| 10 | $CH_3$ | n-$C_4H_9$ | n-$C_4H_9$ | | | |
| 11 | n-$C_4H_9$ | n-$C_4H_9$ | n-$C_4H_9$ | | | |
| 12 | $CH_3$ | $CH_3$ | i-$C_4H_9$ | | | |
| 13 | $CH_3$ | i-$C_4H_9$ | i-$C_4H_9$ | | | |
| 14 | $CH_3$ | $CH_3$ | $CH_3$ | | | |

-continued

| | | | | | | | |
|---|---|---|---|---|---|---|---|
| 15 | $CH_3$ | $t-C_4H_9$ | $t-C_4H_9$ | | | | |
| 16 | $CH_3$ | $CH_3$ | Vinyl | | | | |
| 17 | $CH_3$ | Vinyl | Vinyl | | | | |
| 18 | $CH_3$ | $CH_3$ | Allyl | | | | |
| 19 | $CH_3$ | Allyl | Allyl | | | | |
| 20 | $CH_3$ | $CH_3$ | Ethynyl | | | | |
| 21 | $CH_3$ | $CH_3$ | Propargyl | | | | |
| 22 | $CH_3$ | $CH_3$ | Phenyl | 0.40; 7.0–7.5 | | 3.70 | 6.5–7.8 |
| 23 | $CH_3$ | $C_2H_5$ | Phenyl | | | | |
| 24 | $CH_3$ | Phenyl | Phenyl | | | | |
| 25 | $CH_3$ | $CH_3$ | o-Tolyl | | | | |
| 26 | $CH_3$ | $CH_3$ | m-Tolyl | | | | |
| 27 | $CH_3$ | $CH_3$ | p-Tolyl | | | | |
| 28 | $CH_3$ | $CH_3$ | p-Ethyl-phenyl | | | | |
| 29 | $CH_3$ | $CH_3$ | m-Isopropyl-phenyl | | | | |
| 30 | $CH_3$ | $CH_3$ | p-Isopropyl-phenyl | | | | |
| 31 | $CH_3$ | $CH_3$ | m-Isobutyl-phenyl | | | | |
| 32 | $CH_3$ | $CH_3$ | m-tert.-Butyl-phenyl | | | | |
| 33 | $CH_3$ | $CH_3$ | p-tert.-Butyl-phenyl | | | | |
| 34 | $CH_3$ | $CH_3$ | o-Chlorophenyl | | | | |
| 35 | $CH_3$ | $CH_3$ | m-Chlorophenyl | | | | |
| 36 | $CH_3$ | $CH_3$ | p-Chlorophenyl | | | | |

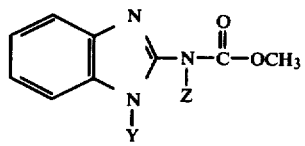

| | Y = $SiR^1R^2R^3$ | | | Z = $SiR^1R^2R^3$ | | | NMR data (δ in ppm) | | |
|---|---|---|---|---|---|---|---|---|---|
| No. | $R^1$ | $R^2$ | $R^3$ | $R^1$ | $R^2$ | $R^3$ | $SiR^1R^2R^3$ | $OCH_3$ | aromatic |
| 37 | $C_2H_5$ | $C_2H_5$ | $C_2H_5$ | $C_2H_5$ | $C_2H_5$ | $C_2H_5$ | 0.4–1.5 | 3.32 | 6.6–7.4 |
| 38 | $CH_3$ | $CH_3$ | $C_2H_5$ | $CH_3$ | $CH_3$ | $C_2H_5$ | | | |
| 39 | $CH_3$ | $C_2H_5$ | $C_2H_5$ | $CH_3$ | $C_2H_5$ | $C_2H_5$ | | | |
| 40 | $CH_3$ | $CH_3$ | $CH_3$ | $CH_3$ | $CH_3$ | $CH_3$ | | | |
| 41 | $CH_3$ | $CH_3$ | $n-C_3H_7$ | $CH_3$ | $CH_3$ | $n-C_3H_7$ | | | |
| 42 | $CH_3$ | $n-C_3H_7$ | $n-C_3H_7$ | $CH_3$ | $n-C_3H_7$ | $n-C_3H_7$ | | | |
| 43 | $CH_3$ | $i-C_3H_7$ | $i-C_3H_7$ | $CH_3$ | $i-C_3H_7$ | $i-C_3H_7$ | | | |
| 44 | $CH_3$ | $CH_3$ | $i-C_3H_7$ | $CH_3$ | $CH_3$ | $i-C_3H_7$ | | | |
| 45 | $i-C_3H_7$ | $i-C_3H_7$ | $i-C_3H_7$ | $i-C_3H_7$ | $i-C_3H_7$ | $i-C_3H_7$ | | | |
| 46 | $CH_3$ | $n-C_4H_9$ | $n-C_4H_9$ | $CH_3$ | $n-C_4H_9$ | $n-C_4H_9$ | | | |
| 47 | $n-C_4H_9$ | $n-C_4H_9$ | $n-C_4H_9$ | $n-C_4H_9$ | $n-C_4H_9$ | $n-C_4H_9$ | | | |
| 48 | $CH_3$ | $CH_3$ | $i-C_4H_9$ | $CH_3$ | $CH_3$ | $i-C_4H_9$ | | | |
| 49 | $CH_3$ | $i-C_4H_9$ | $i-C_4H_9$ | $CH_3$ | $i-C_4H_9$ | $i-C_4H_9$ | | | |
| 50 | $CH_3$ | $CH_3$ | $t-C_4H_9$ | $CH_3$ | $CH_3$ | $t-C_4H_9$ | 0.55; 0.90 | 3.35 | 6.6–7.4 |
| 51 | $CH_3$ | $t-C_4H_9$ | $t-C_4H_9$ | $CH_3$ | $t-C_4H_9$ | $t-C_4H_9$ | | | |
| 52 | $CH_3$ | $CH_3$ | Vinyl | $CH_3$ | $CH_3$ | Vinyl | | | |
| 53 | $CH_3$ | Vinyl | Vinyl | $CH_3$ | Vinyl | Vinyl | | | |
| 54 | $CH_3$ | $CH_3$ | Allyl | $CH_3$ | $CH_3$ | Allyl | | | |
| 55 | $CH_3$ | Allyl | Allyl | $CH_3$ | Allyl | Allyl | | | |
| 56 | $CH_3$ | $CH_3$ | Ethynyl | $CH_2$ | $CH_2$ | Ethynyl | | | |
| 57 | $CH_3$ | $CH_3$ | Propargyl | $CH_3$ | $CH_3$ | Propargyl | | | |
| 58 | $CH_3$ | $CH_3$ | Phenyl | $CH_3$ | $CH_3$ | Phenyl | 0.40; 7.0–7.5 | 3.2 | 6.5–7.8 |
| 59 | $CH_3$ | $C_2H_5$ | Phenyl | $CH_3$ | $C_2H_5$ | Phenyl | | | |
| 60 | $CH_3$ | Phenyl | Phenyl | $CH_3$ | Phenyl | Phenyl | | | |
| 61 | $CH_3$ | $CH_3$ | o-Tolyl | $CH_3$ | $CH_3$ | o-Tolyl | | | |
| 62 | $CH_3$ | $CH_3$ | m-Tolyl | $CH_3$ | $CH_3$ | m-Tolyl | | | |
| 63 | $CH_3$ | $CH_3$ | p-Tolyl | $CH_3$ | $CH_3$ | p-Tolyl | | | |
| 64 | $CH_3$ | $CH_3$ | p-Ethyl-phenyl | $CH_3$ | $CH_3$ | p-Ethyl-phenyl | | | |
| 65 | $CH_3$ | $CH_3$ | m-Iso-propyl-phenyl | $CH_3$ | $CH_3$ | m-Isopropylphenyl | | | |
| 66 | $CH_3$ | $CH_3$ | p-Iso-propyl-phenyl | $CH_3$ | $CH_3$ | p-Isopropylphenyl | | | |
| 67 | $CH_3$ | $CH_3$ | m-Iso-butylphenyl | $CH_3$ | $CH_3$ | m-Isobutyl-phenyl | | | |
| 68 | $CH_3$ | $CH_3$ | p-Iso-butylphenyl | $CH_3$ | $CH_3$ | p-Isobutyl-phenyl | | | |
| 69 | $CH_3$ | $CH_3$ | m-tert.-Butyl-phenyl | $CH_3$ | $CH_3$ | m-tert.-Butylphenyl | | | |
| 70 | $CH_3$ | $CH_3$ | p-tert.- | $CH_3$ | $CH_3$ | p-tert.- | | | |

| | | | Butyl-phenyl | | | Butylphenyl |
|---|---|---|---|---|---|---|
| 71 | CH₃ | CH₃ | o-Chloro-phenyl | CH₃ | CH₃ | o-Chloro-phenyl |
| 72 | CH₃ | CH₃ | m-Chloro-phenyl | CH₃ | CH₃ | m-Chloro-phenyl |
| 73 | CH₃ | CH₃ | p-Chloro-phenyl | CH₃ | CH₃ | p-Chloro-phenyl |

The active ingredients according to the invention have a strong fungitoxic action. They are particularly suitable for combating harmful phycomycetes, ascomycetes and fungi imperfecti, e.g., *Plasmopara viticola* in vines, *Phytophthora infestans* in tomatoes and potatoes, *Erysiphe graminis* in wheat, *Erysiphe cichoriacearum* in cucumbers, *Uncinula necator* in vines, *Podosphaera leucotricha* in apples, *Botrytis cinerea* in vines, strawberries, ornamentals and Solanaceae, *Septoria nodorum* in wheat, *Septoria glycines* in soybeans, *Cercosporella herpotrichoides* in wheat, *Cercospora personata* in groundnuts, *Diplodia natalensis* in citruses, *Pullularia pullulans, Sclerophoma pityophila, Chaetomium globosum* and *Humicola grisea*.

Where the new compounds are employed to protect crop plants, it is advantageous to use fungicidal agents prepared therefrom which contain from 0.1 to 95, preferably from 0.5 to 90, wt% of active ingredient. The application rates depend on the effect desired, and range from 0.01 to 3 kg and more, but preferably from 0.01 and 1 kg of active ingredient per hectare.

The compounds are applied by spraying or dusting the plants with them or treating the seed with them. They may be applied before or after the plants or seed which have been infected by the fungi.

Where the active ingredients are used to protect materials, e.g., as fungicides for paints, application rates are from 0.25 to 5% of active ingredient, based on the total weight of the paint. Other materials which may be preserved or microbicidally treated are glues, adhesives, plastics dispersions, sealants, paper, textiles, leather, raw skins, and plastics, especially polyurethane and soft PVC.

The new active ingredients may also be used as fungicidally active components of oily wood preservatives for protecting wood against wood-discoloring fungi; the formulations employed in these instances generally contain from 0.5 to 2 wt% of active ingredient. The agents are applied by treating the wood with them, e.g., by impregnation or painting.

The compounds of the invention can be converted into the conventional formulations, e.g. solutions, emulsions, suspensions, dusts, powders, pastes and granules. The form of application depends entirely on the purpose for which the agents are being used; it should, however, ensure a fine and uniform distribution of the active ingredient. The formulations are prepared in the conventional manner, for example by diluting the active ingredient with solvents and/or carriers, with or without the addition of emulsifiers and dispersants and, where water is used as the diluent, with or without an organic auxiliary solvent. Suitable auxiliaries are, essentially, solvents, for example aromatics, e.g. xylene and benzene, chloroaromatics, e.g. chlorobenzene, paraffins, e.g. petroleum fractions, alcohols, e.g. methanol and butanol, amines, e.g. ethanolamine and dimethylformamide, and water; carriers, for example natural rock powders, e.g. kaolin, alumina, talc and chalk, and synthetic rock powders, e.g. highly disperse silica and silicates; emulsifiers, for example non-ionic and anionic emulsifiers, e.g. polyoxyethylene fatty alcohol esters, alkylsulfonates and arylsulfonates, and dispersants, for example lignin, sulfite waste liquors and methylcellulose.

The formulations, and the ready-to-use preparations obtained therefrom, e.g. solutions, emulsions, suspensions, powders, dusts, pastes or granules, are applied in the conventional manner, e.g. by spraying, atomizing, dusting, treating seed, or watering.

Examples of formulations are given below.

I. 90 parts by weight of compound 1 is mixed with 10 parts by weight of N-methyl-α-pyrrolidone. A mixture is obtained which is suitable for application in the form of very fine drops.

II. 10 parts by weight of compound 1 is dissolved in a mixture consisting of 90 parts by weight of xylene, 6 parts by weight of the adduct of 8 to 10 moles of ethylene oxide with 1 mole of oleic acid-N-monoethanolamide, 2 parts by weight of the calcium salt of dodecylbenzenesulfonic acid, and 2 parts by weight of the adduct of 40 moles of ethylene oxide with 1 mole of castor oil.

III. 20 parts by weight of compound 2 is dissolved in a mixture consisting of 40 parts by weight of cyclohexanone, 30 parts by weight of isobutanol, and 20 parts by weight of the adduct of 40 moles of ethylene oxide with 1 mole of castor oil. By pouring the solution into 100,000 parts by weight of water and finely distributing it therein, an aqueous dispersion is obtained containing 0.02% by weight of the active ingredient.

IV. 20 parts by weight of compound 2 is dissolved in a mixture consisting of 25 parts by weight of cyclohexanol, 65 parts by weight of a mineral oil fraction having a boiling point between 210° and 280° C., and 10 parts by weight of the adduct of 40 moles of ethylene oxide with 1 mole of castor oil. By pouring the solution into 100,000 parts by weight of water and uniformly distributing it therein, an aqueous dispersion is obtained containing 0.02% by weight of the active ingredient.

V. 80 parts by weight of compound 3 is well mixed with 3 parts by weight of the sodium salt of diisobutyl-naphthalene-α-sulfonic acid, 10 parts by weight of the sodium salt of a lignin-sulfonic acid obtained from a sulfite waste liquor, and 7 parts by weight of powdered silica gel, and triturated in a hammer mill. By uniformly distributing the mixture in 20,000 parts by weight of water, a spray liquor is obtained containing 0.4% by weight of the active ingredient.

VI. 3 parts by weight of compound 4 is intimately mixed with 97 parts by weight of particulate kaolin. A dust is obtained containing 3% by weight of the active ingredient.

VII. 30 parts by weight of compound 37 is intimately mixed with a mixture consisting of 92 parts by weight of powdered silica gel and 8 parts by weight of paraffin oil which has been sprayed onto the surface of this silica gel. A formulation of the active ingredient is obtained having good adherence.

VIII. 40 parts by weight of compound 50 is intimately mixed with 10 parts of the sodium salt of a phenolsulfonic acid-urea-formaldehyde condensate, 2 parts of silica gel and 48 parts of water to give a stable aqueous dispersion. Dilution in 100,000 parts by weight of water gives an aqueous dispersion containing 0.04% of active ingredient.

IX. 20 parts of compound 2 is intimately mixed with 2 parts of the calcium salt of dodecylbenzenesulfonic acid, 8 parts of a fatty alcohol polyglycol ether, 2 parts of the sodium salt of a phenolsulfonic acid-urea-formaldehyde condensate and 68 parts of a paraffinic mineral oil. A stable oily dispersion is obtained.

The active ingredients may also be mixed with other, prior art, fungicides. In many instances, the spectrum of fungicidal action is also increased. Synergistic effects also occur with a number of these fungicidal mixtures, i.e., the fungicidal action of the combination product is greater than that of the individual components added together.

Examples of fungicides which can be combined with the compounds of the invention are: dithiocarbamates and their derivatives, e.g. iron(III) dimethyldithiocarbamate, zinc dimethyldithiocarbamate, manganese N,N-ethylene-bis-dithiocarbamate, manganese zinc N,N-ethylenediamine-bis-dithiocarbamate, zinc N,N-ethylene-bis-dithiocarbamate, tetramethylthiuram disulfide, the ammonia complex of zinc N,N-ethylene-bis-dithiocarbamate and zinc N,N'-propylene-bis-dithiocarbamate, and the ammonia complex of zinc N,N'-propylene-bis-dithiocarbamate and N,N'-polypropylene-bis-(thiocarbamoyl)-disulfide; nitro derivatives, e.g. dinitro-(1-methylheptyl)-phenyl crotonate, 2-sec.-butyl-4,6-dinitrophenyl-3,3-dimethylacrylate and 2-sec.-butyl-4,6-dinitrophenyl isopropyl carbonate; heterocyclic compounds, e.g. N-trichloromethylthiotetrahydrophthalimide, N-trichloromethylthio-phthalimide, 2-heptadecyl-2-imidazoline acetate, 2,4-dichloro-6-(o-chloroanilino)-s-triazine, O,O-diethyl pththalimidophosphonothioate, 5-amino-1-(bis-(dimethylamino)-phosphinyl)-3-phenyl-1,2,4-triazole, 5-ethoxy-3-trichloromethyl-1,2,4-thiadiazole, 2,3-dicyano-1,4-dithiaanthraquinone, 2-thio-1,3-dithio-(4,5-b)-quinoxaline, methyl 1-(butylcarbamoyl)-2-benzimidazole-carbamate, 2-methoxycarbonylamino-benzimidazole, 2-thiocyanatomethylthio-benzthiazole, 4-(2-chlorophenylhydrazono)-3-methyl-5-isoxazolone, pyridine-2-thio-1-oxide, 8-hydroxyquinoline and its copper salt, 2,3-dihydro-5-carboxanilido-6-methyl-1,4-oxathiine-4,4-dioxide, 2,3-dihydro-5-carboxanilido-6-methyl-1,4-oxathiine, 2-fur-2-yl-benzimidazole, piperazine-1,4-diyl-bis-(1-(2,2,2-trichloroethyl)-formamide), 2-thiazol-4-yl-benzimidazole, 5-butyl-2-dimethylamino-4-hydroxy-6-methyl-pyrimidine, bis-(p-chlorophenyl)-3-pyridinemethanol, 1,2-bis-(3-ethoxycarbonyl-2-thioureido)-benzene, 1,2-bis-(3-methoxycarbonyl-2-thioureido)-benzene and various fungicides, e.g. dodecylguanidine acetate, 3-(2-(3,5-dimethyl-2-hydroxycyclohexyl)-2-hydroxyethyl)-glutarimide, hexachlorobenzene, N-dichlorofluoromethylthio-N',N'-dimethyl-N-phenyl-sulfuric acid diamide, 2,5-dimethyl-furan-3-carboxylic acid anilide, 2,5-dimethylfuran-3-carboxylic acid cyclohexylamide, 2-methyl-benzoic acid anilide, 2-iodo-benzoic acid anilide, 1-(3,4-dichloroanilino)-1-formylamino-2,2,2-trichloroethane, 2,6-dimethyl-N-tridecyl-morpholine and its salts, 2,6-dimethyl-N-cyclododecyl-morpholine and its salts, diisopropyl 5-nitroisophthalate, 1-(1',2',4'-triazol-1'-yl)-[-(4'-chlorophenoxy)]-3,3-dimethylbutan-2-one, 1-(1',2',4'-triazol-1'-yl)-[1-(4'-chlorophenoxy)]-3,3-dimethylbutan-2-ol, N-(n-propyl)-N-(2,4,6-trichlorophenoxyethyl)-N'-imidazolyl-urea, N-cyclohexyl-N-methoxy-2,5-dimethylfuran-3-carboxamide, 2,4,5-trimethylfuran-3-carboxanilide, 5-methyl-5-vinyl-3-(3,5-dichlorophenyl)-2,4-dioxo-1,3-oxazolidine, 5-methoxymethyl-5-methyl-3-(3,5-dichlorophenyl)-2,4-dioxo-1,3-oxazolidine, and N-[3-(p-tert-butylphenyl-2-methylpropyl]-cis-2,6-dimethylmorpholine.

The following examples illustrate the biological action of the new compounds of the formula I. The agent used for comparison purposes is the fungicidal active ingredient 2-(methoxy-carbonylamino)-benzimidazole (R. Wegler, Chemie der Pflanzenschutz- und Schädlingsbekämpfungsmittel, Vol. 4, p. 175, Springer-Verlag, Berlin, 1977).

EXAMPLE A

Fungicidal action on *Phytophthora infestans* in tomatoes

Leaves of tomato plants of the "Grosse Fleischtomate" variety are sprayed with aqueous suspensions containing 0.05 and 0.025 wt% of the active ingredient. After the sprayed-on liquor has dried, the leaves are infected with a zoospore suspension of *Phytophthora infestans*. The plants are than placed in a steam-saturated chamber at from 16° C. to 18° C. After 5 days, the disease has spread on the untreated but infected plants to such an extent that the fungicidal action of the compounds can be assessed.

| Compound no. | Leaf attack after spraying with liquor containing compound in amounts of | |
|---|---|---|
| | 0.05% | 0.025% |
| 2 | 2 | 2-3 |
| 4 | 1 | 2 |
| 50 | 1 | 1 |
| 2-(Methoxy-carbonylamino)-benzimidazole (comparative agent) | 4 | 5 |
| Control (untreated) | | 5 |

0 = no fungus attack, graduated down to
5 = total attack

EXAMPLE B

Action on *Botrytis cinerea* in pimientos

Pimiento seedlings of the "Neusiedler Ideal Elite" variety were sprayed, after 4 to 5 leaves were well developed, to runoff with 0.1 and 0.05 wt% aqueous liquors containing (dry basis) 80% of active ingredient and 20% of sodium ligninsulfonate. After the sprayed-on layer had dried, the plants were sprinkled with a conidial suspension of the fungus *Botrytis cinerea*, and placed at 22° to 24° C. in a chamber of high humidity to obtain optimum conditions for promoting fungus growth. After 5 days, the disease had spread to such a great extent on the untreated plants that the necroses covered the major portion of the leaves.

| Compound no. | Leaf necroses after spraying with liquor containing compound in amounts of | |
|---|---|---|
| | 0.1% | 0.05% |
| 2 | 0 | 1 |
| 3 | 0 | 1 |
| 4 | 0 | 1 |
| 50 | 0 | 1 |
| Control (untreated) | | 5 |

0 = no necroses, graduated down to
5 = ½ of leaf surface covered with necroses

EXAMPLE C

Action on *Chaetomium globosum* and *Pullularia pullulans*

Filter paper discs 13 mm in diameter and 1 mm thick are impregnated with 0.2 ml of solutions containing 800, 400 or 200 parts of active ingredient per million parts of solution (ppm). The discs are then placed on a 50% malt extract agar in Petri dishes which have previously been inoculated with spores of the fungi *Chaetomium globosum* and *Pullularia pullulans*. The dishes are then incubated for 3 days at from 22° to 24° C. After this time, the fungi in the control dishes have spread very well; the fungicidal action of the active ingredients is assessed in the following manner from the fungus-free zones (halos) which have formed round the filter paper:

| Compound | Assessment of fungicidal action ppm of compound in solution | | |
|---|---|---|---|
| | 800 | 400 | 200 |
| *Chaetomium globosum* | +++ | +++ | +++ |
| 2 | +++ | +++ | +++ |
| 3 | +++ | +++ | +++ |
| 4 | +++ | +++ | +++ |
| 37 | +++ | +++ | +++ |
| 50 | +++ | +++ | +++ |
| Control (no fungicide) | — | | |
| *Pullaria pullulans* | | | |
| 2 | +++ | +++ | +++ |
| 3 | +++ | +++ | +++ |
| 37 | +++ | +++ | +++ |
| 50 | +++ | +++ | +++ |
| Control (no fungicide) | — | | |

— no halo (no fungicidal action)
+ halo less than 1 mm in width (slight fungicidal action)
++ average halo from 1 to 5 mm in width (good fungicidal action)
+++ halo wider than 5 mm (excellent fungicidal action)

We claim:

1. A silyl-benzimidazole-2-carbamic acid ester of the formula

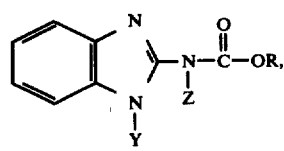

(I)

where Y and Z are hydrogen or a silyl radical of the formula

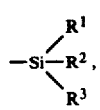

where $R^1$, $R^2$ and $R^3$ independently of one another are unsubstituted or halogen-substituted alkyl, alkenyl or alkynyl of up to 12 carbon atoms, cycloalkyl of up to 7 carbon atoms which is unsubstituted or substituted by alkyl or alkynyl of up to 4 carbon atoms, or phenyl which is unsubstituted or substituted by halogen or alkyl of up to 4 carbon atoms, and R is alkyl of up to 4 carbon atoms, with the proviso that Y and Z are not both hydrogen.

2. A silyl-benzimidazole-2-carbamic acid ester of the formula I as claimed in claim 1, wherein Y and/or Z denote a silyl radical of the formula

where $R^1$, $R^2$ and $R^3$ independently of one another are alkyl of from 1 to 4 carbon atoms.

3. Methyl N-triethylsilyl benzimidazole-2-carbamate.

4. Methyl N-(dimethyl-n-butylsilyl)-benzimidazole-2-carbamate.

5. Methyl N-(dimethyl-tert-butylsilyl)-benzimidazole-2-carbamate.

6. Methyl N,N'-bis-(triethylsilyl)-benzimidazole-2-carbamate.

7. Methyl N,N'-bis-(dimethyl-n-butylsilyl)-benzimidazole-2-carbamate.

8. Methyl N,N'-bis-(dimethyl-tert-butylsilyl)-benzimidazole-2-carbamate.

9. A fungicidal formulation consisting essentially of a liquid or solid carrier and a fungicidally effective amount of a silyl-benzimidazole-2-carbamic acid ester of the formula

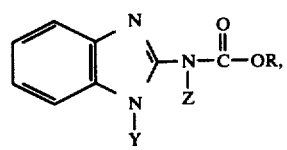

(I)

where Y and Z are hydrogen or a silyl radical of the formula

where $R^1$, $R^2$ and $R^3$ independently of one another are unsubstituted or halogen-substituted alkyl, alkenyl or alkynyl of up to 12 carbon atoms, cycloalkyl of up to 7 carbon atoms which is unsubstituted or substituted by alkyl or alkynyl of up to 4 carbon atoms, or phenyl which is unsubstituted or substituted by halogen or alkyl of up to 4 carbon atoms, and R is alkyl of up to 4 carbon atoms, with the proviso that Y and Z are not both hydrogen.

10. A method of combating fungi which comprises applying to the fungi or to areas, plants or seed threatened by fungus attack a fungicidally effective amount of a silyl-benzimidazole-2-carbamic acid ester of the formula

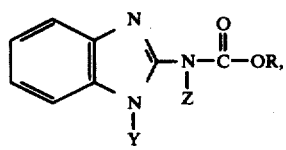 (I)

where Y and Z are hydrogen or a silyl radical of the formula

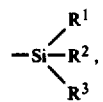

where $R^1$, $R^2$ and $R^3$ independently of one another are unsubstituted or halogen-substituted alkyl, alkenyl or alkynyl of up to 12 carbon atoms, cycloalkyl of up to 7 carbon atoms which is unsubstituted or substituted by alkyl or alkynyl of up to 4 carbon atoms, or phenyl which is unsubstituted or substituted by halogen or alkyl of up to 4 carbon atoms, and R is alkyl of up to 4 carbon atoms, with the proviso that Y and Z are not both hydrogen.